United States Patent
Sathyanarayana (10) Patent No.: US 7,729,533 B2
(45) Date of Patent: Jun. 1, 2010

(54) SYSTEMS AND METHODS FOR PRODUCING CLASSIFIERS WITH INDIVIDUALITY

(75) Inventor: Shashidhar Sathyanarayana, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 932 days.

(21) Appl. No.: 11/531,133

(22) Filed: Sep. 12, 2006

(65) Prior Publication Data

US 2008/0063265 A1    Mar. 13, 2008

(51) Int. Cl.
  *G06K 9/62* (2006.01)
  *G06K 9/00* (2006.01)
(52) U.S. Cl. ..................... 382/159; 382/133
(58) Field of Classification Search .......... 382/133, 382/159, 181, 197, 224, 282; 707/7
  See application file for complete search history.

(56) References Cited

U.S. PATENT DOCUMENTS

| | | | |
|---|---|---|---|
| 4,958,375 A | 9/1990 | Reilly et al. | |
| 5,299,284 A | 3/1994 | Roy | |
| 5,325,445 A * | 6/1994 | Herbert | 382/225 |
| 5,680,476 A | 10/1997 | Schmidt et al. | |
| 5,930,392 A | 7/1999 | Ho | |
| 5,995,651 A | 11/1999 | Gelenbe et al. | |
| 6,009,199 A * | 12/1999 | Ho | 382/224 |
| 6,238,342 B1 | 5/2001 | Feleppa et al. | |
| 6,631,204 B1 | 10/2003 | Smith | |
| 6,855,114 B2 | 2/2005 | Drukker et al. | |
| 6,996,549 B2 | 2/2006 | Zhang et al. | |
| 7,074,188 B2 * | 7/2006 | Nair et al. | 600/443 |
| 7,171,042 B2 | 1/2007 | Hartmann et al. | |
| 7,421,114 B1 * | 9/2008 | Brandt | 382/159 |
| 7,471,832 B2 * | 12/2008 | Luo et al. | 382/224 |
| 2002/0067857 A1 | 6/2002 | Hartmann et al. | |

(Continued)

FOREIGN PATENT DOCUMENTS

WO    WO 2005/088521 A1    9/2005

(Continued)

OTHER PUBLICATIONS

Redpath D.B. et al: "Boosting Feature Selection" Pattern Recognition and Data Mining Lecture Notes in Computer Science; LNCS, Springer-Verlag, BE, vol. 3686, 2005, pp. 305-334.

(Continued)

*Primary Examiner*—Daniel G Mariam
(74) *Attorney, Agent, or Firm*—Frommer Lawrence & Haug LLP; Bruce E. Black (57) ABSTRACT

The systems and methods of the invention described herein improve classification accuracy by producing classifiers with individuality, in which each classifier exhibits its own distinctive behavior. A method according to one exemplary embodiment produces each classifier with individuality by randomly selecting subsets of a feature vector and using the randomly selected subsets of the feature vector in the design of the classifier. Because different subsets of the feature vector are used for each classifier, each classifier exhibits its own distinctive behavior or individuality. The classifiers with individuality improve classification accuracy, for example, when used as classifiers in a classifier array. This is because the individuality among the classifiers in the array ensures that a misclassification committed by one of the classifiers will not be repeated by other classifiers in the array, thereby improving the overall accuracy of the classifier array.

10 Claims, 6 Drawing Sheets

U.S. PATENT DOCUMENTS

| | | |
|---|---|---|
| 2005/0213825 A1 | 9/2005 | Basak et al. |
| 2006/0078315 A1* | 4/2006 | Wada et al. .................. 386/117 |
| 2006/0116734 A1* | 6/2006 | Dobak et al. ................... 607/27 |
| 2009/0116734 A1* | 5/2009 | Willis .......................... 382/159 |

OTHER PUBLICATIONS

Kestler, H.A.; Mussel, C: "An Empirical Comparison of Feature Reduction Methods in The Context of Microarray Data Classification" Proceedings of: Artificial Neural Networks in Pattern Recognition. Second IAPR Workshop, ANNPR 2006, Aug. 31 Sep. 2, 2006 Ulm, Germany, Sep. 2, 2006 pp. 260-273.

Pujol O et al Institute of Electrical and Electronics Engineers: "Near Real-Time Plague Segmentation of IVUS" Computers in Cardiology 2003. Thessaloniki, Greece, Sep. 21-24, 2003, New York, NY: IEEE, US, vol. 30, Sep. 21, 2003 pp. 69-72.

Duda, R.; Hart P., Stork D.: "Pattern Classification, Chapter 9: Algorithm-Independent Machine Learning" 2001, John Wiley & Sons, New York.

* cited by examiner

FIG. 4B

SYSTEMS AND METHODS FOR PRODUCING CLASSIFIERS WITH INDIVIDUALITY

FIELD OF THE INVENTION

The field of the invention relates to classifiers, and more particularly, to systems and methods for producing classifiers with individuality.

BACKGROUND

In the field of pattern recognition, classifiers are used to classify an object into one of a number of predefined classes or categories. For example, classifiers may be used to classify a loan applicant as either a high risk or a low risk. Other applications for classifiers include speech recognition, face recognition, image processing, and medical diagnosis.

Classifiers are used in image processing to classify pixels or regions in an image into one of a number of predefined classes. For example, a classifier may be used to classify regions in an image of natural scenery into one of a number of classes such as leaves, grass, or sky. In the medical field, classifiers are used to classify regions in images of patients into different types of tissue, for example, abnormal or diseased tissue and normal tissue.

Classification typically involves extracting a set of features of an object called a feature vector. A feature can be any characteristic or property of the object that provides useful information of the object's class. The feature may be in the form of a numeric measurement of a characteristic or property of the object. For example, a feature of a loan applicant may be the applicant's monthly income. A classifier uses the feature vector of the object to classify the object into one of a number of predefined classes or categories.

A classifier can be customized for a particular classification problem by training the classifier to identify particular classes. This usually involves a training phase, in which the classifier is presented with a set of example objects that are representative of known classes. The classifier extracts features of the example objects and learns to associate these features with the known classes of the objects based on association rules. Once the classifier has been trained to identify the classes, the classifier can be used to identify occurrences of these classes in new objects.

In practice, classifiers misclassify objects some of the time. Therefore, there is a need to improve classification accuracy.

SUMMARY

The systems and methods of the invention described herein improve classification accuracy by producing classifiers with individuality, in which each classifier exhibits its own distinctive behavior. A method according to one exemplary embodiment produces each classifier with individuality by randomly selecting subsets of a feature vector and using the randomly selected subsets of the feature vector in the design of the classifier. Because different subsets of the feature vector are used for each classifier, each classifier exhibits its own distinctive behavior or individuality.

The classifiers with individuality improve classification accuracy, for example, when used as classifiers in a classifier array. This is because the individuality among the classifiers in the array ensures that a misclassification committed by one of the classifiers will not be repeated by other classifiers in the array, thereby improving the overall accuracy of the classifier array.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention may be gleaned in part by study of the accompanying figures, in which like reference numerals refer to like segments.

DETAILED DESCRIPTION

The invention provides systems and methods for designing classifiers with individuality, in which each classifier exhibits its own distinctive behavior.

Figure 1A:
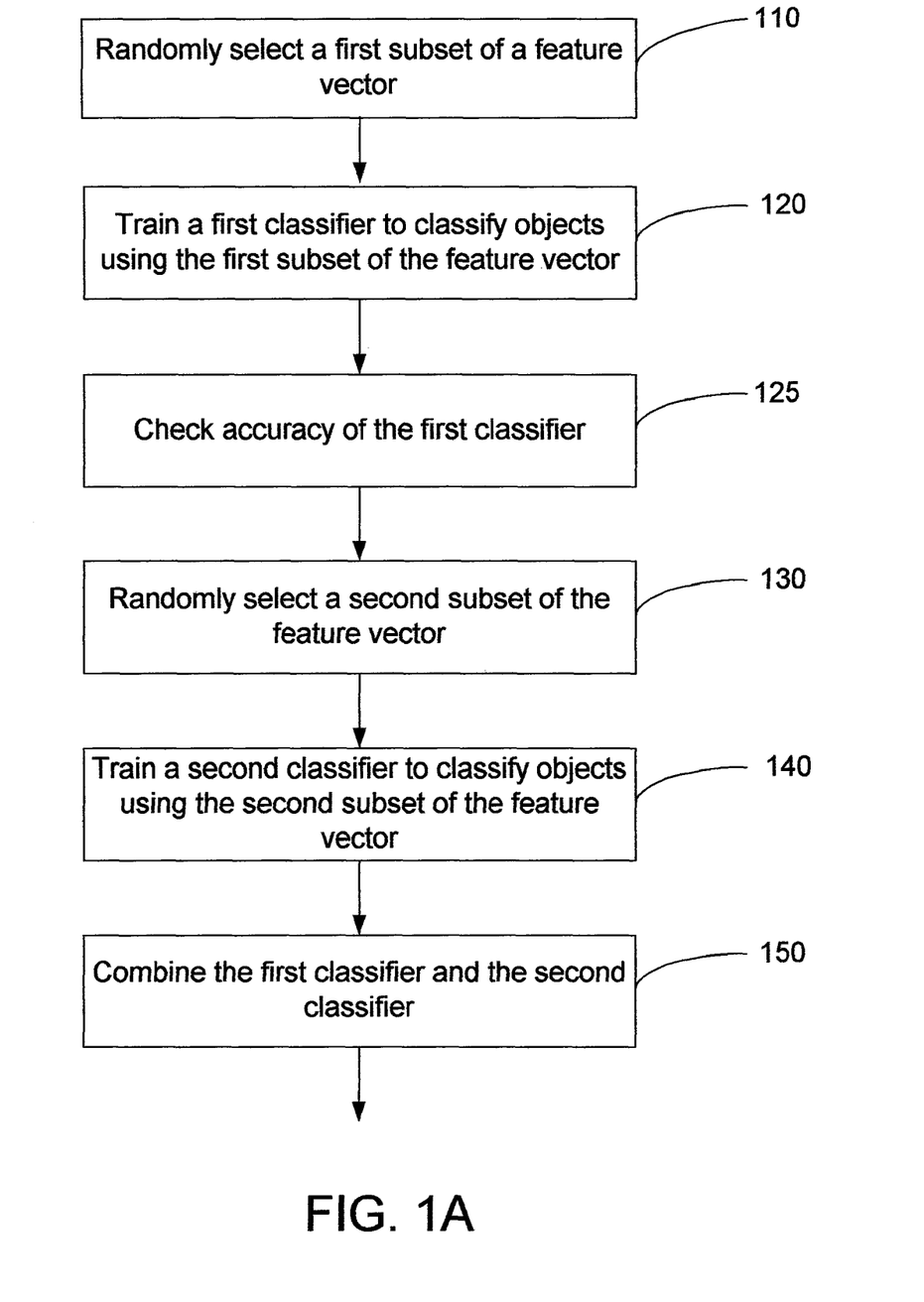
FIGS. 1A and 1B show a block diagram of one exemplary method of designing a classifier with individuality.
Figure 1B:
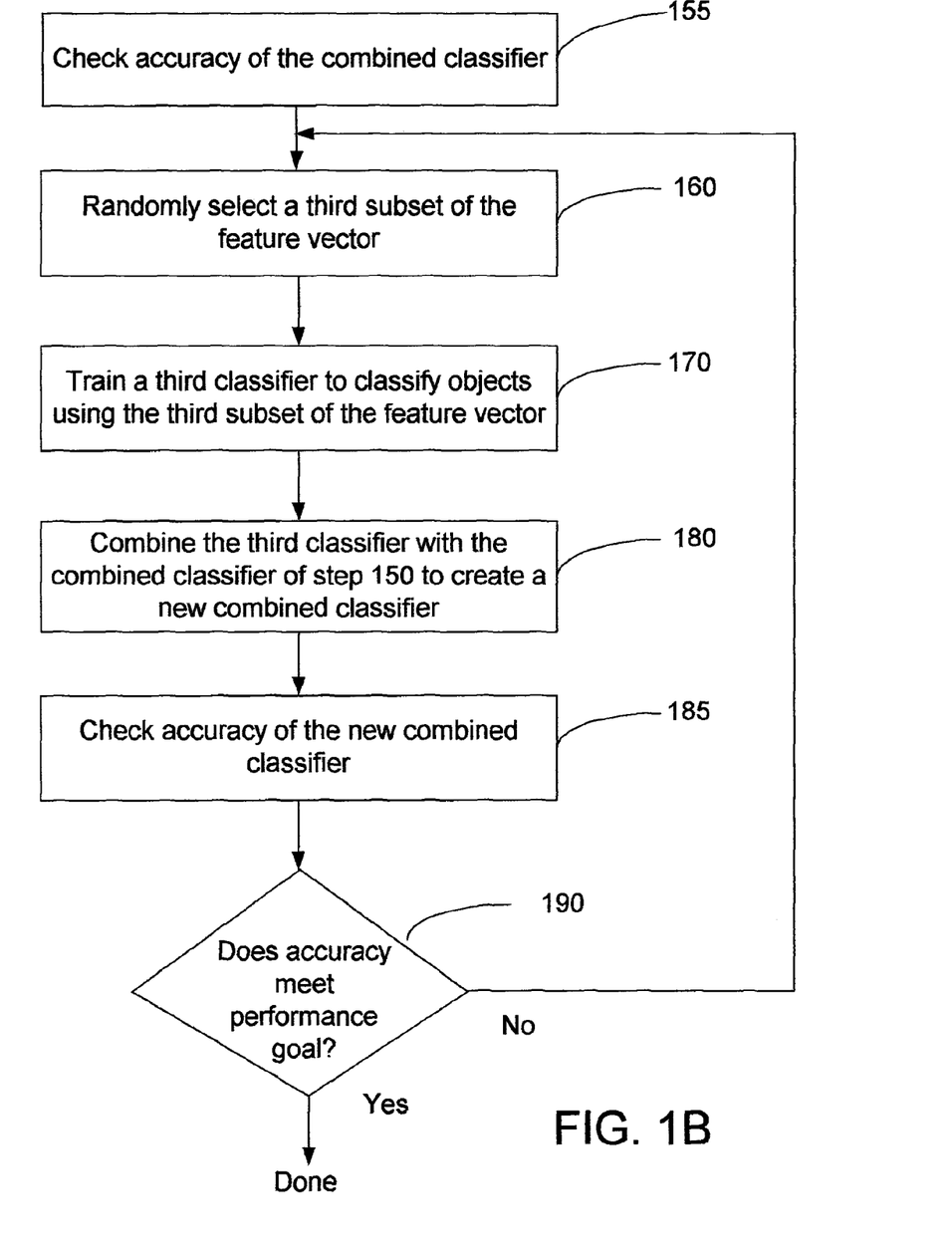

FIGS. 1A and 1B show a block diagram of one exemplary method of designing a classifier with individuality. In step 110, a first subset of features is randomly selected from a feature vector. For example, an n-dimensional feature vector x may be represented as feature vector $x=[x_1, x_2, \ldots, x_n]$ where $x_1, x_2, \ldots, x_n$ represent the set of features making up the feature vector. In step 110 a subset of the features $x_1, x_2, \ldots, x_n$ of the feature vector is selected.

In step 120, a first classifier, e.g., a linear classifier, is trained to classify objects using the first subset of the feature vector. This may be done by presenting the first classifier with a set of example objects of known classes. The first classifier extracts the first subset of the feature vector from the objects and learns to associate the first subset of the feature vector of the objects with the known classes of the objects.

In step 125, the accuracy of the first classifier is checked, e.g., by presenting the first classifier with the set of example objects and recording which objects the first classifier correctly classifies and which objects the first classifier misclassifies.

In step 130, a second subset of features is randomly selected from the feature vector. The second subset may have the same number of features as the first subset or not.

In step 140, a second classifier with a weighted input is trained to classify objects using the second subset of the feature vector. The second classifier may be trained with the same set of example objects used to train the first classifier. Preferably, the input of the second classifier is weighted to give more weight to objects that the first classifier misclassified than to objects that the first classifier correctly classified. For example, the second classifier may give 80% weight to the objects that the first classifier misclassified and 20% weight to the objects that the first classifier correctly classified. This ensures that the second classifier attempts to correct the mistakes committed by the first classifier.

In step 150, the first classifier and the second classifier are combined. This may be done by fusion of the two classifiers, which is known in the art, or any other technique known in the art.

In step 155, the accuracy of the combined classifier is checked, e.g., by presenting the combined classifier with the set of example objects and recording which objects the combined classifier correctly classifies and which objects the combined classifier misclassifies.

In step 160, a third subset of features is randomly selected from the feature vector.

In step 170, a third classifier with a weighted input is trained to classify objects using the third subset of the feature vector. The third classifier may be trained with the same set of example objects used to train the first and second classifiers. Preferably, the input of the third classifier is weighted to give more weight to objects that the combined classifier misclassified than to objects that the combined classifier correctly classified. This ensures that the third classifier attempts to correct mistakes committed by the combined classifier of step 150.

In step 180, the third classifier is combined with the combined classifier of step 150 to create a new combined classifier. The new combined classifier may be realized, e.g., by voting among the first, second, and third classifiers, in which an object is classified based on the classification assigned to the object by a majority of the classifiers.

In step 185, the accuracy of the new combined classifier is checked, e.g., by presenting the new combined classifier with the set of example objects and determining the classification accuracy rate.

In step 190, the accuracy of the new combined classifier is compared to a performance goal, e.g., 90% classification accuracy. If the performance goal is meet, then the design is complete and the new combined classifier of step 180 becomes a classifier with individuality. If the performance goal is not meet, then steps 160-190 are repeated and another classifier is added. Steps 160-190 may be repeated until the performance goal is meet or until no significant improvement in accuracy is observed by adding more classifiers.

Since each of the first, second and third classifiers looks at a different random subset of the feature vector, the resulting combined classifier has a distinctive behavior or individuality. The combined classifier is used as one classifier with individuality.

The method of FIGS. 1A and 1B is one embodiment for designing classifiers with individuality. In other embodiments, the second and third classifiers may weigh all objects equally instead of having weighted inputs. Also, the random selection of subsets of the feature vector does not have to be completely random. For example, specific rules may be built into the random selection to achieve desired effects.

Figure 2:
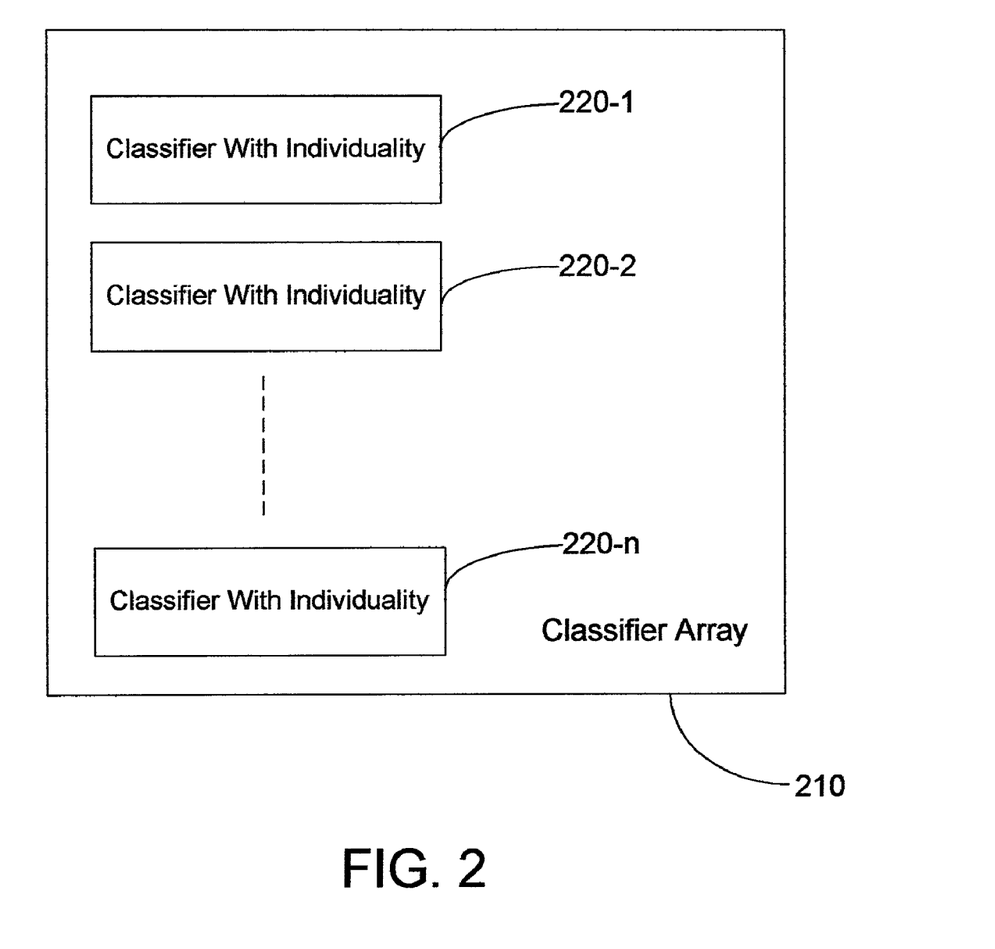
FIG. 2 is a diagram of a classifier array comprising classifiers with individuality.

The classifiers with individuality may be used in a classifier array to improve classification accuracy. FIG. 2 is a diagram of a classifier array 210 comprising classifiers with individuality 220-1 to 210-n ("220-1-n"). In one embodiment, an object is classified by having each classifier 220-1-n in the array 210 separately classify the object, performing a vote among the classifiers 220-1-n in the array 210, and classifying the object based on the classification assigned to the object by a majority of classifiers 220-1-n. Each classifier 220-1-n in the classifier array 210 is designed using the method of the invention, in which different subsets of the feature vector are randomly selected for each classifier 220-1-n. Alternatively, a combination of classifiers with individuality and conventional classifiers may be used in the array.

The classifiers with individuality 220-1-n enhance the accuracy of the classifier array 210 because each classifier 220-1-n brings in its unique expertise to the classification task. The individuality among the classifiers 220-1-n in the array 210 ensures that a misclassification committed by one of the classifiers 220-1-n will not be repeated by other classifiers 220-1-n in the array 210, and will therefore be "voted out" by the other classifiers 220-1-n.

Figure 3:
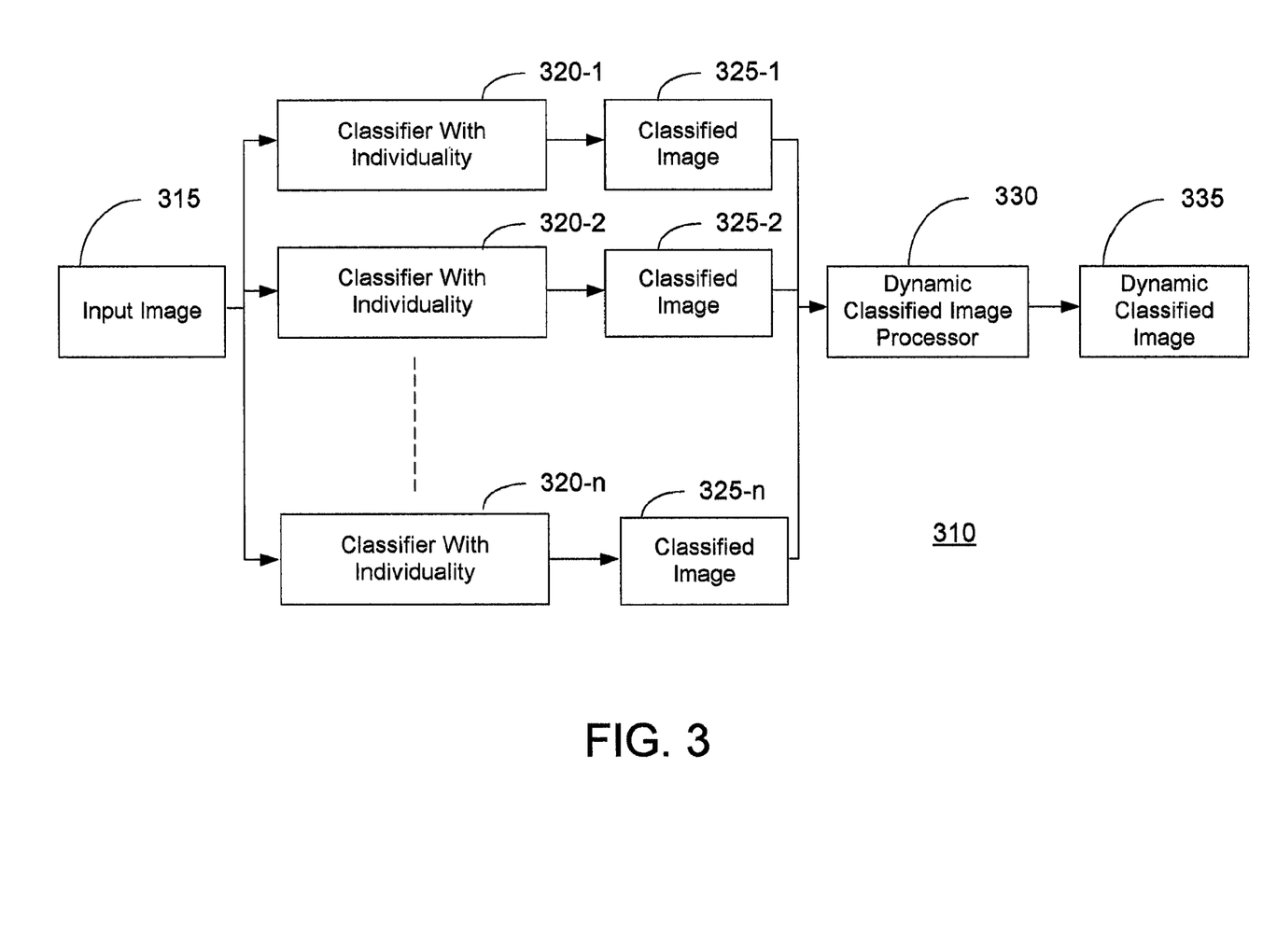
FIG. 3 is a functional block diagram of a dynamic classifier comprising classifiers with individuality.

The classifiers with individuality may also be used in a dynamic classifier, which is described in patent application Ser. No. 10/940,359, entitled "Systems And Methods For Producing A Dynamic Classified Image," filed on Sep. 13, 2004, the entire specification of which is incorporated by reference. FIG. 3 is a functional block diagram of a dynamic classifier 310 using classifiers with individuality. The dynamic classifier 310 comprises an image input 315, a plurality or array of classifiers with individuality 320-1 to 320-n ("320-1-n"), and a dynamic classified image processor 330. The image input 315 may originate from an imaging device, computer memory, an image processor, or the like.

In operation, each of the classifiers with individuality 320-1-n classifies the input image 315 into a classified image 325-1-n, in which regions of the input image 315 are classified. For example, each classified image 325-1-n may be color-coded, in which the different classes are represented by different colors. The classified images 325-1-n are inputted to the dynamic classified image processor 330, which sequentially outputs the classified images 325-1-n to a display device (not shown). The sequentially display of the classified images 325-1-n produces a dynamic classified image 335, in which the classification of the input image 315 varies with time depending on which one of the classified images 325-1-n is displayed at a given instant. The dynamic classified image processor 330 may continuously cycle through the classified images 325-1-n at a rate, e.g., of 10 to 30 classified images 325-1-n a second.

The classifiers 320-1-n and the dynamic classified image processor 330 may be implemented on different processors, the same processor, or a combination thereof. For example, the classifiers 320-1-n may be implemented as a set of programs, where each program defines the computational procedure for one of the classifiers 320-1-n. The classifiers 320-1-n and the dynamic classified image processor 330 may then be implemented on the same processor by having the processor sequentially execute the program for each of the classifiers 320-1-n. In this implementation, the different classifiers 320-1-n are sequentially applied to the input image 315 by the processor.

The dynamic classified image 335 provides dynamic stimuli that encourages the visual system of a human observer to excuse occasional classification errors from a minority of the classified images 325-1-n and retain the generally correct classifications from a majority of the classified images 325-1-n. The individuality among the classifiers 320-1-n ensures that a misclassification committed by one of the classifiers 320-1-n will not be repeated by other classifiers 320-1-n in the dynamic classifier 310.

The method of the invention can also be applied to the field of intravascular ultrasound (IVUS) imaging. In IVUS imaging, an ultrasound transducer emits ultrasonic waves in the body which are reflected back to the transducer by tissues in the body. The transducer converts the reflected ultrasonic waves into electrical signals, which are processed by the ultrasound system into an ultrasound image of the body. The electrical signals associated with different types of tissue exhibit different radio frequency (RF) spectrums. Therefore, the RF spectrum of tissue provides useful information of the tissue's type, and can therefore be used by a classifier to classify tissue.

For example, the RF spectrum of tissue may comprise, e.g., 64 measurements, where each measurement represents the energy of the reflected ultrasonic wave at a different frequency range. The measurements may be grouped into frequency bins, where each frequency bin corresponds to a different frequency range.

Figure 4A:
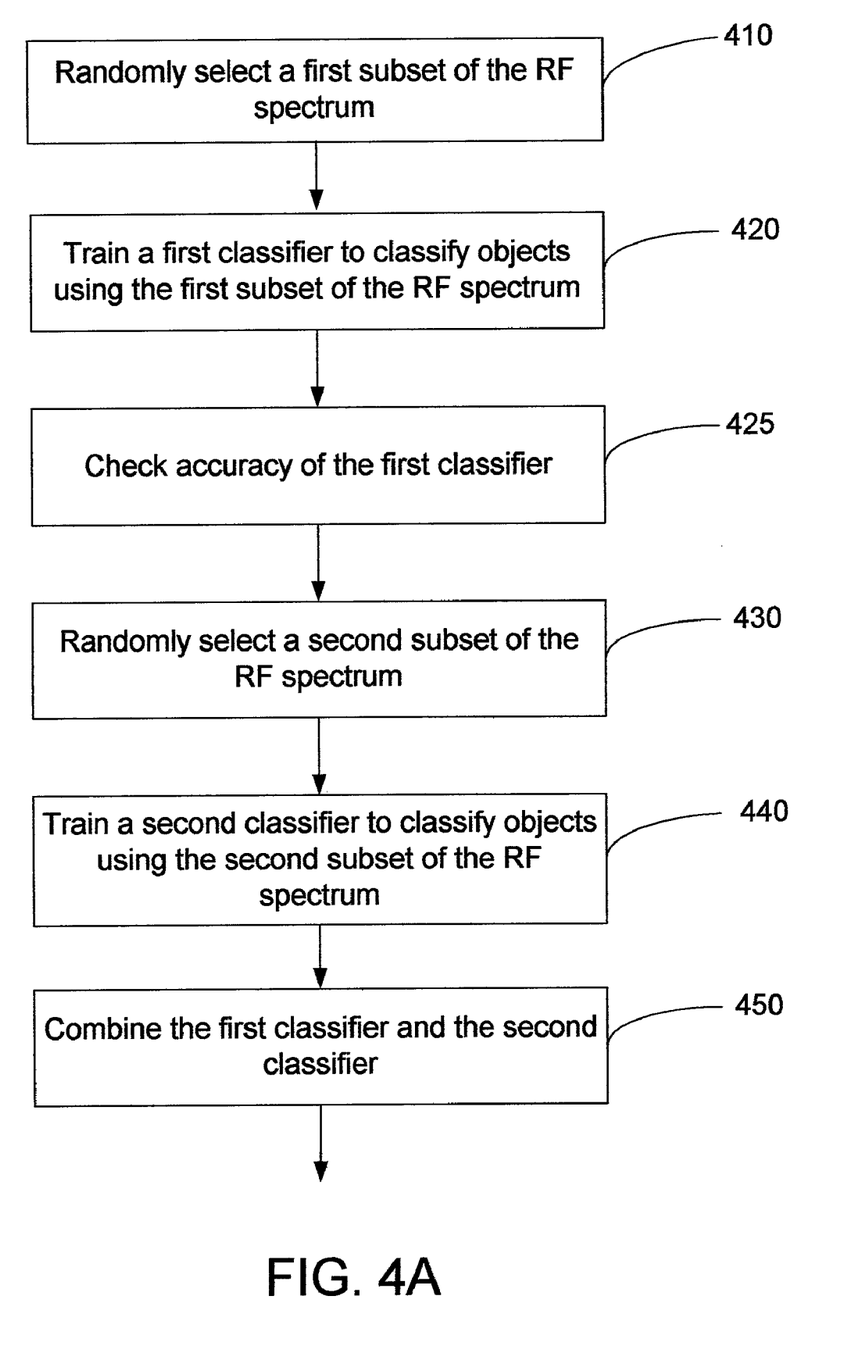
FIGS. 4A and 4B show a block diagram of one exemplary method of designing a classifier with individuality for ultrasound imaging applications.
Figure 4B:
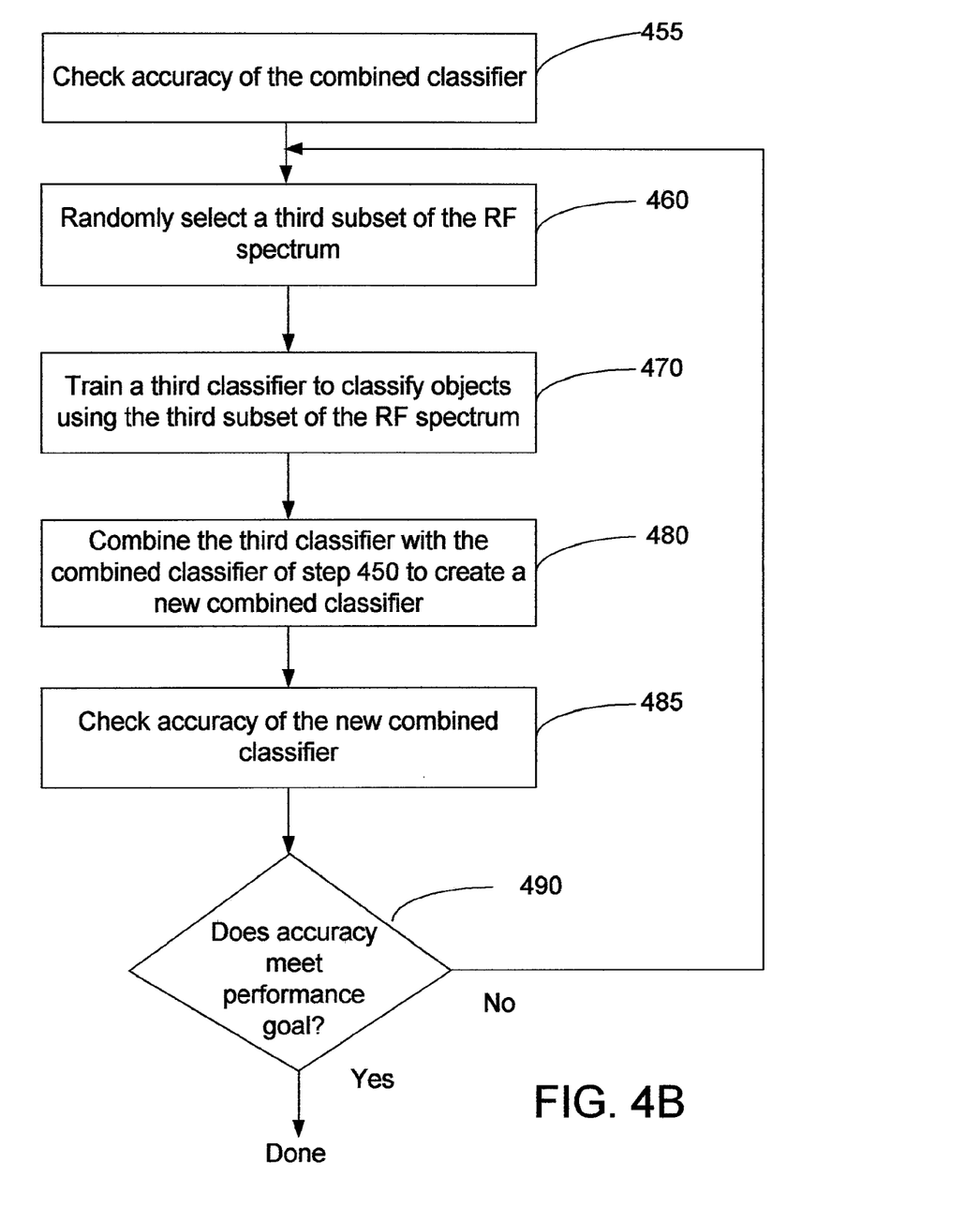

FIGS. 4A and 4B show a block diagram of one exemplary method of designing a classifier with individuality for ultrasound imaging applications. In step 410, a first subset of frequency bins is randomly selected from the RF spectrum. For example, the first subset of the RF spectrum may comprise three frequency bins while the full RF spectrum may comprise 64 frequency bins.

In step 420, a first classifier, e.g., a linear classifier, is trained to classify tissues using the first subset of the RF spectrum, e.g., three frequency bins. This may be done by presenting the first classifier with a set of RF spectrums of example tissues of known classes. Because the first classifier uses the first subset of the RF spectrum, the first classifier only looks at the portions of the RF spectrums of the example tissues corresponding to the first subset.

In step 425, the accuracy of the first classifier is checked, e.g., by presenting the first classifier with the set of RF spectrums of the example tissues and recording which tissues the first classifier correctly classifies and which tissues the first classifier misclassifies.

In step 430, a second subset of frequency bins, e.g., three frequency bins, is randomly selected from the RF spectrum.

In step 440, a second classifier with a weighted input is trained to classify tissues using the second subset of the RF spectrum. The second classifier may be trained with the same set of RF spectrums of the example tissues used to train the first classifier. Preferably, the input of the second classifier is weighted to give more weight to tissues that the first classifier misclassified than to tissues that the first classifier correctly classified. This ensures that the second classifier attempts to correct the mistakes committed by the first classifier.

In step 450, the first classifier and the second classifier are combined. This may be done by fusion of the two classifiers, which is known in the art, or any other technique known in the art.

In step 455, the accuracy of the combined classifier is checked, e.g., by presenting the combined classifier with the set of RF spectrums of the example tissues and recording which tissues the combined classifier correctly classifies and which tissues the combined classifier misclassifies.

In step 460, a third subset of frequency bins, e.g., three frequency bins, is randomly selected from the RF spectrum.

In step 470, a third classifier with a weighted input is trained to classify tissues using the third subset of the RF spectrum. The third classifier may be trained with the same set of RF spectrums of the example tissues used to train the first and second classifiers. Preferably, the input of the third classifier is weighted to give more weight to tissues that the combined classifier misclassified than to tissues that the combined classifier correctly classified. This ensures that the third classifier attempts to correct mistakes committed by the combined classifier of step 450.

In step 480, the third classifier is combined with the combined classifier of step 450 to create a new combined classifier. The new combined classifier may be realized, e.g., by voting among the first, second, and third classifiers, in which tissue is classified based on the classification assigned to the tissue by a majority of the classifiers.

In step 485, the accuracy of the new combined classifier is checked, e.g., by presenting the new combined classifier with the set of RF spectrums of the example tissues and determining the classification accuracy rate.

In step 490, the accuracy of the new combined classifier is compared to a performance goal. If the performance goal is meet, then the design is complete and the new combined classifier of step 480 becomes a classifier with individuality. If the performance goal is not meet, then steps 460-490 are repeated until the performance goal is meet or until no significant improvement in accuracy is observed by adding more classifiers.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. For example, a classifier array or a dynamic classifier may use a combination of classifiers with individuality and conventional classifiers. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A method for classifying ultrasound images, the method comprising:
    providing a plurality of ultrasound images, each ultrasound image having a corresponding RF spectrum;
    randomly selecting a first subset of frequency bins from the RF spectrum;
    training a first classifier to classify objects using the first subset of frequency bins;
    checking accuracy of the first classifier in classifying objects;
    randomly selecting a second subset of frequency bins from the RF spectrum;
    training a second classifier to classify objects using the second subset of frequency bins;
    weighing an input to the second classifier to give greater weight to objects that the first classifier misclassifies than to objects that the first classifier correctly classifies;
    combining the first and second classifiers into a combined classifier;
    classifying an object by applying the combined classifier to the object; and
    displaying a classified image based on the classification by the combined classifier.

2. The method of claim 1, wherein the first classifier is a linear classifier.

3. The method of claim 1, further comprising:
    randomly selecting a third subset of frequency bins from the RF spectrum;
    training a third classifier to classify objects using the third subset of frequency bins; and
    combining the third classifier with the combined classifier.

4. The method of claim 3, further comprising:
    checking accuracy of the combined classifier in classifying objects; and
    weighing an input of the third classifier to give greater weight to objects that the combined classifier misclassifies than to objects that the combined classifier correctly classifies.

5. The method of claim 1, wherein the plurality of classifiers are linear classifiers.

6. The method of claim 1, wherein the classified image comprises a color-coded region in which different classes are represented by different colors.

7. A method for classifying ultrasound images, the method comprising:
- providing a plurality of ultrasound images, each ultrasound image having a corresponding RF spectrum;
- randomly selecting a subset of frequency bins from the RF spectrum for each one of a plurality of classifiers;
- training each one of the plurality of classifiers to classify objects using the respective subset of the frequency bins;
- classifying an object with each of the plurality of classifiers;
- performing a vote among the plurality of classifiers;
- classifying the object based on the classification assigned to the object by a majority of the votes of the plurality of classifiers; and
- displaying a classified image based on the majority of votes.

8. A method for classifying ultrasound images, comprising:
- processing a common input image using a plurality of classifiers, wherein each classifier produces a classified image based on the common input image, and each classifier uses different subsets of a feature vector to classify the common input image; and
- displaying the classified images from the plurality of classifiers using a dynamic classified image processor, the dynamic classified image processor being coupled to the plurality of classifiers.

9. The method of claim 8, wherein displaying the classified images comprises displaying the classified images at a rate of between 10 to 30 classified images a second.

10. The system of claim 8, wherein displaying the classified images comprises displaying the classified images in a random order.

* * * * *